(12) United States Patent
Collazo

(10) Patent No.: US 10,299,929 B2
(45) Date of Patent: May 28, 2019

(54) BONE VOID FORMING APPARATUS

(71) Applicant: Howmedica Osteonics Corp., Mahwah, NJ (US)

(72) Inventor: Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 504 days.

(21) Appl. No.: 14/992,726

(22) Filed: Jan. 11, 2016

(65) Prior Publication Data

US 2016/0199071 A1 Jul. 14, 2016

Related U.S. Application Data

(60) Provisional application No. 62/102,260, filed on Jan. 12, 2015.

(51) Int. Cl.
| | |
|---|---|
| *A61B 17/17* | (2006.01) |
| *A61B 17/16* | (2006.01) |
| *A61F 2/30* | (2006.01) |
| *A61F 2/38* | (2006.01) |
| *A61F 2/36* | (2006.01) |
| *A61F 2/40* | (2006.01) |

(Continued)

(52) U.S. Cl.
CPC ............. *A61F 2/30* (2013.01); *A61B 17/164* (2013.01); *A61B 17/1675* (2013.01); *A61B 17/1764* (2013.01); *A61F 2/30734* (2013.01); *A61F 2/3676* (2013.01); *A61F 2/389* (2013.01); *A61F 2/3859* (2013.01); *A61F 2/4059* (2013.01); *A61B 17/1725* (2013.01); *A61B 2090/062* (2016.02); *A61F 2002/2835* (2013.01); *A61F 2002/2892* (2013.01); *A61F 2002/30738* (2013.01); *A61F 2002/30774* (2013.01); *A61F 2002/30784* (2013.01); *A61F 2002/30879* (2013.01); *A61F 2002/4077* (2013.01)

(58) Field of Classification Search
CPC ....... A61B 17/16; A61B 17/164; A61B 17/17; A61B 17/1725; A61B 17/1764
See application file for complete search history.

(56) References Cited

U.S. PATENT DOCUMENTS

| 4,065,817 A | 1/1978 | Branemark et al. |
| 4,158,893 A | 6/1979 | Swanson |

(Continued)

FOREIGN PATENT DOCUMENTS

| EP | 0016480 A1 | 10/1980 |
| EP | 2168506 A1 | 3/2010 |

(Continued)

*Primary Examiner* — Christopher Beccia
(74) *Attorney, Agent, or Firm* — Lerner, David, Littenberg, Krumholz & Mentlik, LLP

(57) ABSTRACT

A bone void forming assembly includes a support member having a head portion and an elongate portion extending therefrom. A guide member is connected to the support member and has a guide body including a channel extending therethrough. The channel defines an axis offset and obliquely angled relative to an axis of the elongate portion. The assembly also includes reamer having a cutting head and a stop member. A bushing is slidably connected to the reamer between the stop member and cutting head and is slidably connectable to the guide body via the channel.

17 Claims, 4 Drawing Sheets

(51) Int. Cl.
  *A61B 90/00* (2016.01)
  *A61F 2/28* (2006.01)

(56) References Cited

U.S. PATENT DOCUMENTS

| | | | |
|---|---|---|---|
| 4,693,721 A | 9/1987 | Ducheyne | |
| 4,728,335 A | 3/1988 | Jurgutis | |
| 4,738,256 A | 4/1988 | Freeman et al. | |
| 4,777,942 A | 10/1988 | Frey et al. | |
| 4,790,852 A | 12/1988 | Noiles | |
| 4,822,366 A | 4/1989 | Bolesky | |
| 4,846,839 A | 7/1989 | Noiles | |
| 4,944,757 A | 7/1990 | Martinez et al. | |
| 5,342,363 A * | 8/1994 | Richelsoph | A61B 17/175 128/898 |
| 5,342,366 A | 8/1994 | Whiteside et al. | |
| 5,445,642 A | 8/1995 | McNulty et al. | |
| 5,489,311 A | 2/1996 | Cipolletti | |
| 5,496,324 A | 3/1996 | Barnes | |
| 5,540,694 A * | 7/1996 | DeCarlo, Jr. | A61B 17/175 606/80 |
| 5,906,644 A | 5/1999 | Powell | |
| 5,976,145 A * | 11/1999 | Kennefick, III | A61B 17/175 606/80 |
| 5,976,147 A | 11/1999 | LaSalle et al. | |
| 5,989,257 A | 11/1999 | Tidwell et al. | |
| 6,053,945 A | 4/2000 | O'Neil et al. | |
| 6,071,311 A | 6/2000 | O'Neil et al. | |
| 6,152,963 A | 11/2000 | Noiles et al. | |
| 6,214,052 B1 | 4/2001 | Burkinshaw | |
| 6,494,913 B1 * | 12/2002 | Huebner | A61F 2/40 606/87 |
| 6,702,822 B1 | 3/2004 | Noiles et al. | |
| 6,887,276 B2 | 5/2005 | Gerbec et al. | |
| 6,902,583 B2 | 6/2005 | Gerbec et al. | |
| 7,074,224 B2 | 7/2006 | Daniels et al. | |
| 7,090,677 B2 | 8/2006 | Fallin et al. | |
| 7,255,702 B2 | 8/2007 | Serra et al. | |
| 7,291,174 B2 | 11/2007 | German et al. | |
| 7,297,163 B2 | 11/2007 | Huebner | |
| 7,393,355 B2 | 7/2008 | Tulkis et al. | |
| 7,481,814 B1 | 1/2009 | Metzger | |
| 7,632,273 B2 | 12/2009 | Schnieders et al. | |
| 7,785,328 B2 | 8/2010 | Christie et al. | |
| 7,799,085 B2 | 9/2010 | Goodfried et al. | |
| 7,806,936 B2 | 10/2010 | Wright | |
| 7,892,288 B2 | 2/2011 | Blaylock et al. | |
| 7,892,290 B2 | 2/2011 | Bergin et al. | |
| 7,918,892 B2 | 4/2011 | Huebner | |
| 7,942,879 B2 | 5/2011 | Christie et al. | |
| 8,029,573 B2 | 10/2011 | Podolsky | |
| 8,052,687 B2 | 11/2011 | Sackett et al. | |
| 8,157,869 B2 | 4/2012 | Metzger et al. | |
| 8,167,882 B2 | 5/2012 | Sackett et al. | |
| 8,177,788 B2 | 5/2012 | McLean et al. | |
| 8,382,849 B2 | 2/2013 | Thomas | |
| 8,424,183 B2 | 4/2013 | Thomas | |
| 8,444,699 B2 | 5/2013 | Metzger et al. | |
| 8,506,645 B2 | 8/2013 | Blaylock et al. | |
| 8,535,385 B2 | 9/2013 | Hanssen et al. | |
| 8,900,317 B2 | 12/2014 | Zubok et al. | |
| 9,011,444 B2 | 4/2015 | Primiano et al. | |
| 9,149,282 B2 | 10/2015 | Servidio et al. | |
| 2001/0009974 A1 | 7/2001 | Reisfeld | |
| 2003/0171756 A1 * | 9/2003 | Fallin | A61B 17/175 606/80 |
| 2004/0092951 A1 | 5/2004 | Serra et al. | |
| 2004/0162619 A1 | 8/2004 | Blaylock et al. | |
| 2004/0267267 A1 | 12/2004 | Daniels et al. | |
| 2005/0288676 A1 | 12/2005 | Schnieders et al. | |
| 2007/0118229 A1 | 5/2007 | Bergin et al. | |
| 2007/0162033 A1 | 7/2007 | Daniels et al. | |
| 2008/0147071 A1 | 6/2008 | Serra et al. | |
| 2008/0161812 A1 | 7/2008 | Sackett et al. | |
| 2008/0306600 A1 | 12/2008 | Huebner | |
| 2010/0082031 A1 | 4/2010 | Sackett et al. | |
| 2010/0114323 A1 | 5/2010 | Deruntz et al. | |
| 2010/0286696 A1 | 11/2010 | Christie et al. | |
| 2011/0190899 A1 | 8/2011 | Pierce et al. | |
| 2012/0089146 A1 | 4/2012 | Ferko et al. | |
| 2012/0226281 A1 | 9/2012 | Sackett et al. | |
| 2014/0276882 A1 | 9/2014 | Collazo et al. | |
| 2014/0277567 A1 | 9/2014 | Collazo et al. | |
| 2015/0190150 A1 | 7/2015 | Primiano et al. | |
| 2015/0366567 A1 | 12/2015 | Servidio et al. | |

FOREIGN PATENT DOCUMENTS

| | | |
|---|---|---|
| EP | 2181672 A1 | 5/2010 |
| GB | 2159416 A | 12/1985 |
| WO | 03094698 A2 | 11/2003 |
| WO | 2008069800 A1 | 6/2008 |
| WO | 2009094698 A1 | 8/2009 |

* cited by examiner

BONE VOID FORMING APPARATUS

CROSS-REFERENCE TO RELATED APPLICATIONS

This application claims the benefit of the filing date of U.S. Provisional Patent Application No. 62/102,260 filed Jan. 12, 2015, the disclosure of which is hereby incorporated herein by reference.

BACKGROUND OF THE INVENTION

Joint replacement surgery is a common orthopedic procedure to repair and replace a damaged, diseased, or otherwise unhealthy joint. These procedures generally fall into two categories: primary and revision. In a primary joint replacement, the operator replaces the native joint with prosthetic components typically by first resecting the native bone and/or cartilage and then affixing the prosthetic components to the resected bone.

A revision procedure is performed to replace the primary prosthesis, or in some instances, a previously implanted revision prosthesis. Typically, during a revision procedure, the previously implanted prosthesis is extracted and the underlying bone resurfaced in preparation for receipt of the revision prosthesis. Bone defects in the form of bone loss or deterioration are frequently exposed upon extraction of the previously implanted prosthesis. These defects often reside within the epiphyseal and metaphyseal regions of the bone and extend radially outwardly from the center of the bone. Such defects may be caused by, inter alia, osteolysis, necrosis, infection, and bone incidentally removed along with the previously implanted prosthesis. In order to account for such defects, numerous void filling implants, such as that disclosed in Noiles U.S. Pat. No. 4,846,839, for example, have been developed to fill the voids formed by these defects and to provide structural support for the bone and prosthesis.

Despite the benefits of these void filling implants, their use in complex revision procedures may further complicate the procedure. Prior to extraction of a previously implanted prosthesis, the joint must be exposed. In an example of a total knee replacement, exposure can be made difficult for a number of reasons, such as an exceptionally tight extensor mechanism, which may be due to an improperly fitted prosthesis. One technique for exposing difficult-to-expose knees is a tibial tubercle osteotomy in which the patella tendon is released from the tibia by resecting the bone surrounding the tibial tubercle, which is later resecured to the tibia by at least one fixation device, such as a bone screw or cerclage wire, for example. However, the presence of a void filler, or even an intramedullary stem, creates an obstacle for the fixation device that must be navigated, oftentimes blind, resulting in increased complication of the procedure.

In another example, a patient may suffer an extensor mechanism complication, such as patellar tendon rupture, that must be repaired during the revision procedure. The ruptured tendon may be repaired by an allograft technique where a bone plug with an attached tendon is secured to the tibia also by a fixation device. Again the presence of a void filler or intramedullary stem may interfere with such a repair.

Therefore there is a need for a void filling prosthesis that facilitates bone-to-bone fixation and tissue-to-bone fixation.

BRIEF SUMMARY OF THE INVENTION

Generally, disclosed herein are devices and methods for filling bone voids and also providing means for soft tissue and/or bone-to-bone fixation.

In one aspect of the disclosure, a void filling prosthesis, includes first and second ends defining a length therebetween and outer and inner surfaces defining a sidewall therebetween. The sidewall is at least partially curved about an axis that extends along the length. The void filling prosthesis also includes a fixation prominence extending from the outer surface and includes a first aperture extending in a direction toward the sidewall.

Additionally, the first aperture may be threaded to receive a threaded fastener. A second aperture may define a passageway extending entirely through the fixation prominence. Furthermore, a third aperture may be disposed adjacent to the first aperture. The second aperture may extend through the fixation prominence between the first and third apertures. Also, the first and third apertures may extend parallel to each other and the second aperture may extend substantially perpendicular to the first and third apertures.

Continuing with this aspect, the inner surface may include a solid material and the outer surface may include a porous material. The fixation prominence may be at least partially comprised of a porous metal material. Also, the void filler may include first and second portions and a channel extending therethrough. The channel may define the inner surface. Further, the first and second portions may each be substantially frustoconical. The void filler may also include at least one notch in the sidewall. The first portion may be configured to fit in a void formed in a metaphysis of a long bone and the second portion may be configured to fit in a void formed in a diaphysis of a long bone. The long bone may be a tibia. The fit of the first portion in the void may be a press-fit.

In another aspect of the disclosure, a void filling prosthesis includes first and second ends and an inner surface disposed therebetween. The inner surface defines a channel that extends through the entirety of the prosthesis and is configured to receive an elongate portion of a joint prosthesis therein. The void filling prosthesis also includes a fixation prominence extending from an outer surface of the prosthesis and has at least one fixation aperture.

Additionally, the at least one fixation aperture may a threaded opening. Also, the channel may extend along a longitudinal axis of the void filling prosthesis and the at least one fixation aperture may extend through the fixation prominence in a direction transverse to the longitudinal axis.

Continuing with this aspect, the at least one fixation aperture may be a plurality of fixation apertures that include a first set of fixation apertures that each have a threaded inner surface and a second set of fixation apertures that are oriented in a direction transverse to the first set of fixation apertures. The first set of fixation apertures may extend partially into the fixation prominence and the second set of fixation apertures extend through the fixation prominence.

In a further aspect of the disclosure, a prosthetic system for implantation into an end of bone includes a first prosthesis having a stem, and a second prosthesis having first and second ends and inner and outer surfaces extending between the first and second ends. The inner surface defines a channel for receipt of the stem. The outer surface has at least one fixation aperture extending therein.

Additionally, the channel may be configured to receive the stem such that a gap sufficiently large to support a cement mantle is formed between the stem and the inner surface of the second prosthesis. The second prosthesis may include a first portion configured to be received within a metaphysis of the bone and a second portion configured to be received within a diaphysis of the bone.

Continuing with this aspect, the second prosthesis may include a fixation prominence extending radially outwardly therefrom. The at least one fixation aperture may extend into the fixation prominence. The fixation prominence may extend along the first and second portions. The fixation prominence may include an intermediate segment that is at least partially cylindrical and the at least one fixation aperture may extend into the intermediate segment. The at least one fixation aperture may be threaded. The fixation prominence may include first and second flanking segments that flank the intermediate segment. The thickness of the void filler is may be greater at the intermediate segment than at the flanking segments.

In a still further aspect of the disclosure, a method of implanting a void filling prosthesis into an end of bone includes inserting a void filling prosthesis into a void in the bone. The void filling prosthesis has first and second ends and a fixation prominence extending therefrom. The fixation prominence has at least one fixation aperture. The method also includes advancing a first fixation device through the bone and at least partially into the fixation aperture.

Additionally, the inserting step may include inserting the void filling prosthesis so that the second end is disposed within the bone and the first end is flush with the end of the bone or disposed within the bone. The fixation aperture and fixation device may be correspondingly threaded. The method may also include reaming a first portion of the bone to receive a first frustoconical portion of the void filling prosthesis, and reaming a second portion of the bone to receive the fixation prominence. The method may also include inserting a body of an aiming device into the first end of the void filling prosthesis. The aiming device may include an aiming arm that has at least one guide aperture. The method may also include aligning the at least one guide aperture with at least one fixation aperture.

In yet a further aspect of the disclosure, a method of implanting a void filling prosthesis into an end of bone includes inserting a void filling prosthesis into a void in the bone. The void filling prosthesis has first and second ends and inner and outer surfaces disposed therebetween. The inner surface defines a channel that extends through the entirety of the prosthesis and is configured to receive an elongate portion of a joint prosthesis. The outer surface includes at least one fixation aperture. The method also includes advancing a first fixation device through the bone and at least partially into the fixation aperture.

Additionally, the method may also include inserting the elongate portion of a joint prosthesis into and through the channel such that at least a portion of the elongate portion extends from the second end of the void filling prosthesis.

BRIEF DESCRIPTION OF THE DRAWINGS

These and other features, aspects, and advantages of the present invention will become better understood with regard to the following description, appended claims, and accompanying drawings where:

DETAILED DESCRIPTION

When referring to specific directions in the following discussion of certain implantable devices, it should be understood that such directions are described with regard to the implantable device's orientation and position during exemplary application to the human body. Thus, as used herein, the term "proximal" means close to the heart and the term "distal" means more distant from the heart. The term "anterior" means toward the front of the body or the face and the term "posterior" means toward the back of the body. The term "medial" means toward the midline of the body and the term "lateral" means away from the midline of the body. Also, as used herein, the terms "about," "generally" and "substantially" are intended to mean that deviations from absolute are included within the scope of the term so modified.

Figure 1:
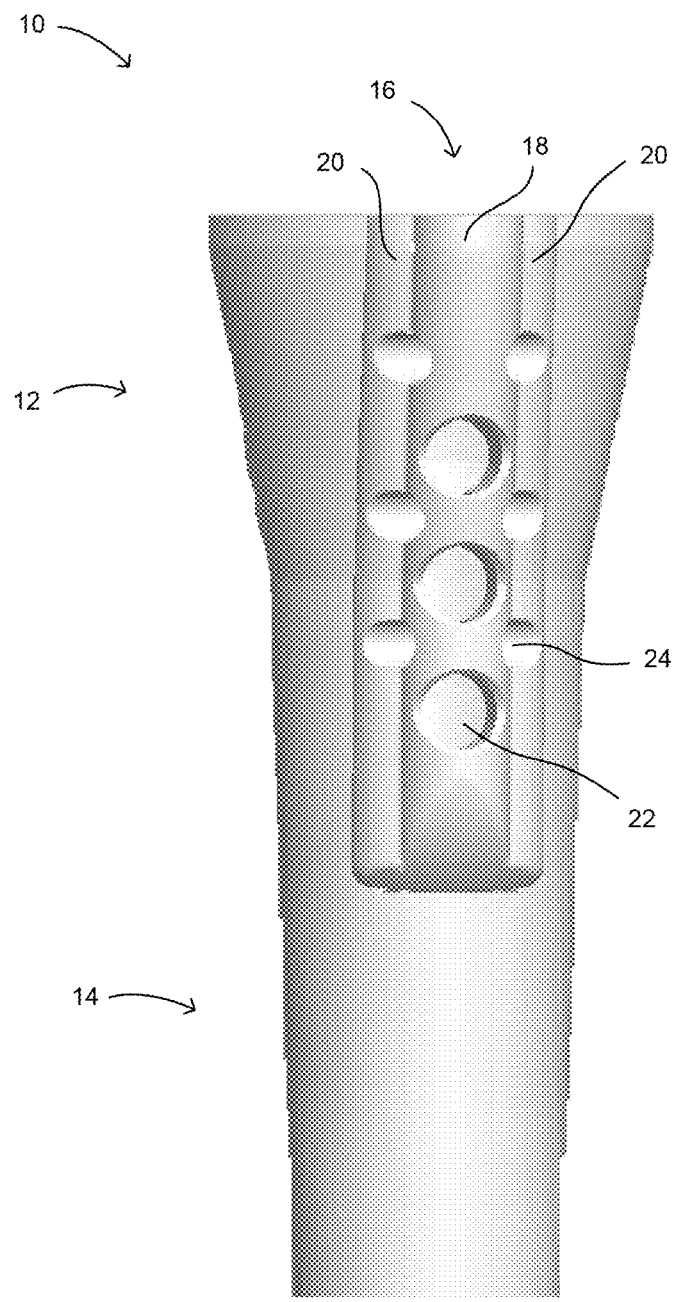
FIG. 1 is a front view of one embodiment of a void filling prosthesis.
Figure 2:
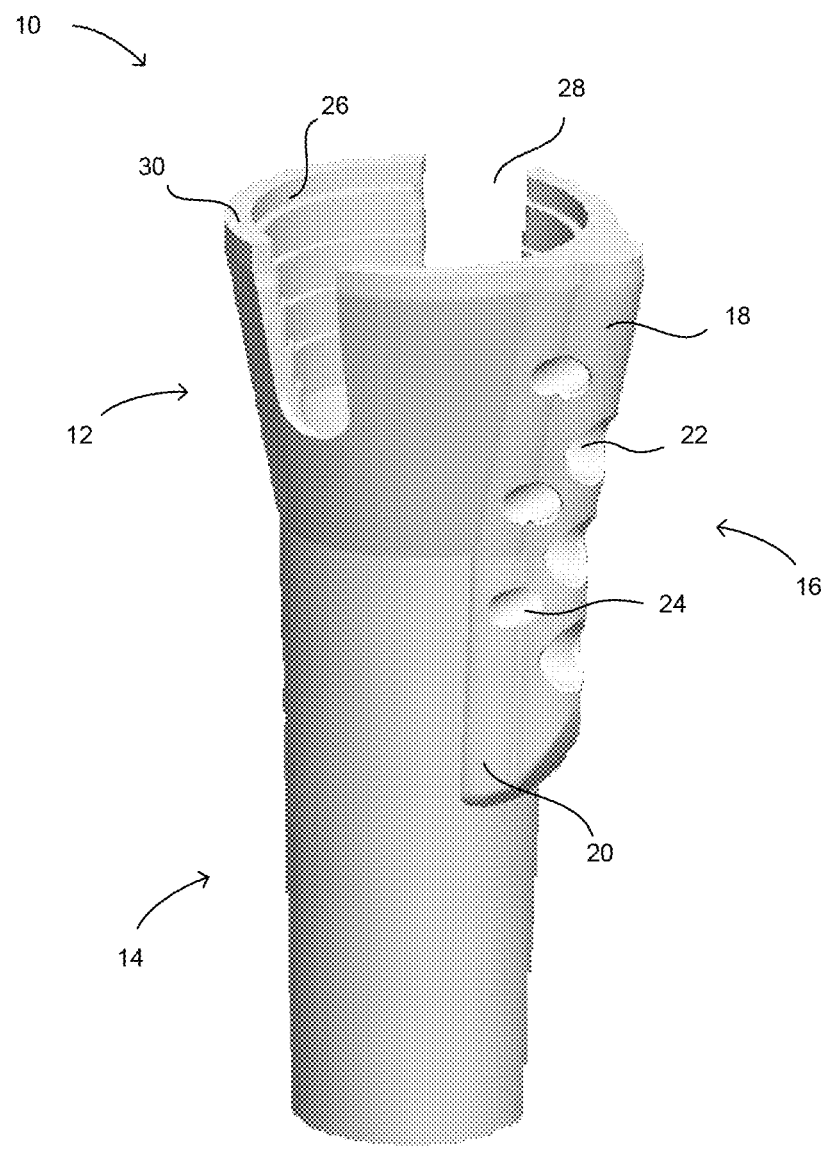
FIG. 2 is a perspective view of the void filling prosthesis of FIG. 1.

FIGS. 1 and 2 depict a void filler 10 or void filling prosthesis that is configured for placement within a void in a tibia and generally includes a metaphyseal portion or first portion 12, a diaphyseal portion or second portion 14, and a fixation prominence 16 that extends along portions of metaphyseal and diaphyseal portions 12 and 14. It is noted that, while the following discussion refers to void filler 10 in relation to a tibia, the same principles apply for a void filler that may be utilized in a proximal humerus or distal or proximal femur. Of course, it is also envisioned that the present invention may have applicability elsewhere in the body.

Metaphyseal portion 12, as shown, is generally frustoconical. However, in some embodiments, metaphyseal portion 12 may be cylindrical. In other embodiments metaphyseal portion 12 may include lobed portions, asymmetrical geometries or other geometries that extend beyond the general frustoconical shape in order to help address asymmetric or lateral and/or medial defects in the bone. Examples of alternate geometrical shapes that can be employed are disclosed in U.S. Publication Nos. 2013/0150858; 2013/0172892; 2014/0276882; and 2014/0277567, the disclosures of which are hereby incorporated-by-reference herein in their entireties.

A channel extends through metaphyseal portion 10 and defines an inner surface 26 and a sidewall 30. Inner surface 26 is preferably a stepped surface or otherwise textured surface to promote bone cement adhesion. Metaphyseal portion 12 also includes notches 28 in sidewall 30 that form a clearance space for a baseplate keel of a tibial component.

Diaphyseal portion 14 is generally cylindrical or frustoconical to substantially match the intramedullary canal of a long bone. In some embodiments, diaphyseal portion 14 may be frustoconical with a cylindrical distal end. Diaphyseal portion 14 extends distally from metaphyseal portion 12, and the channel that extends through metaphyseal portion 12 also extends through diaphyseal portion 14 so that the channel extends through the length of the entirety of void filler 10. The inner surface of diaphyseal portion 14 that is defined by this channel may also be stepped or textured to facilitate cement adhesion. The channel is preferably sized to receive a prosthesis stem and allow for sufficient space to receive and support a cement mantle such as a cement mantle that includes polymethyl methacrylate.

Fixation prominence 16 extends radially outwardly from the outer surface of diaphyseal and metaphyseal portions 12 and 14 and extends along these portions in a general proximal-distal direction. Fixation prominence 16 is preferably located in an area of void filler 10 that would be placed in an anterior or posterior position inside a tibial bone. However, fixation prominence 16 can be located in other locations, such as medial or lateral positions on void filler 10. In some embodiments, fixation prominence 16 may only extend along the metaphyseal portion 12 or diaphyseal portion 14. In other embodiments, there may be multiple fixation prominences 16 extending along void filler 10 in various locations. For example, a fixation prominence 16 may extend along void filler 10 in an anterior, posterior, lateral, and medial position.

Fixation prominence 16 generally includes an intermediate elongate segment 18 and flanking elongate segments 20 (best shown in FIG. 1). Intermediate segment 18 protrudes from the outer surface of void filler 10 further than at flanking segments 20 such that the thickness of void filler 10 at intermediate segment 18 is thicker than at flanking segments 20. This helps maximize the depth of threaded openings 22 extending into intermediate segment 18, while minimizing the amount of space taken up by void filler 10 in the bone.

Intermediate and flanking segments 18 and 20 are generally curved to form cylindrical geometries, which may be complementary to a reaming tool. However, in some embodiments flanking segments 20 may blend into intermediate segment 18 to give the appearance of a single segment. In other, embodiments, segments 18 and 20 may have other geometries, such as square or triangular geometries. At the distal end of fixation prominence 16, intermediate and flanking segments 18 and 20 are tapered to facilitate impaction into an end of bone.

Fixation prominence 16 includes fixation apertures that may be utilized to affix bone to bone and tissue to bone via various fixation means, such as threaded fasteners, cerclage wires, and sutures, for example. One such fixation aperture is a threaded opening 22 located in intermediate segment 18. Intermediate segment 18 includes a plurality of these threaded openings, which extend in a direction transverse to a longitudinal axis of void filler 10 and toward the sidewall/channel of void filler 10. The depth of threaded openings 22 is such that a threaded fastener, such as a bone screw, can be inserted through a segment of bone and into the threaded portion to create solid fixation.

Another fixation aperture is a passageway 24 that extends through fixation prominence 16 in a direction transverse to threaded openings 22. In some embodiments, the transverse direction may be substantially perpendicular with the extent of threaded openings 22. These passageways may be smooth in order to safely house a fixation wire, suture, or other flexible fixation device. Passageways 24 are generally situated or positioned through fixation prominence 16 at locations that are between each of the plurality of threaded openings so that threaded openings 22 and passageways 24 do not intersect.

While fixation prominence 16 is described and depicted as generally elongate and extending along and between diaphyseal and metaphyseal portions 12 and 14, fixation prominence 16 may be another configuration, including, but not limited to, a plurality of bumps extending outwardly from the sidewall of void filler 10 at various locations about void filler 10. Each of these bumps may be square or circular and may each include threaded opening 22 and/or passageway 24 as described above.

Also, it is contemplated that void filler 10 may not include a fixation prominence, but rather threaded openings 22 extending into sidewall 30. In such an embodiment, sidewall 30 may be thicker in order to accommodate a threaded fastener.

In some embodiments, void filler 10 may be implanted into the bone such that fixation prominence 16 faces posteriorly. In such an embodiment, void filler 10 may include circumferential grooves (not shown) within metaphyseal and diaphyseal portions 12 and 14 that allow for a wire or suture to be retained therein, when the wire is wrapped around a portion of void filler 10 from a posterior to anterior direction.

Void filler 10 can be made from any biocompatible material including stainless steel, titanium, cobalt-chromium, tantalum, niobium, or polymeric material such as PEEK. In addition, the void filler's bone contacting surfaces may be made from a porous metal such as titanium foam, and the void filler's non-bone contacting surfaces, such as inner surface 26, may be made from solid or nonporous metal. The porosity of the bone contacting surfaces allows for bony ingrowth therein. In some embodiments, the entire thickness of void filler 10 may be porous, while in other embodiments, the entire thickness of void filler 10 may be solid.

With particular regard to the construction of fixation prominence 16, fixation prominence 16 may be entirely porous while the interior of threaded apertures 22 and passageways 24 may be coated with a solid material. In some embodiments, threaded openings 22 may be lined with a material softer than that of a threaded fastener, which deforms to conform to the threaded fastener upon insertion therein. In other embodiments, fixation prominence 16 may be primarily solid while the outer surface is treated to provide the requisite porosity. As an example, such treatment may be performed by high energy beam processing, such as Selective Laser Melting ("SLM") and Electron Beam Melting ("EBM"), or other additive manufacturing processes. Examples of high energy beam processing are disclosed in U.S. Pat. Nos. 7,537,664 and 8,728,387 and U.S. Publication Nos. 2006/0147332 and 2013/0268085, the disclosures of which are hereby incorporated-by-reference herein in their entireties.

Figure 3:
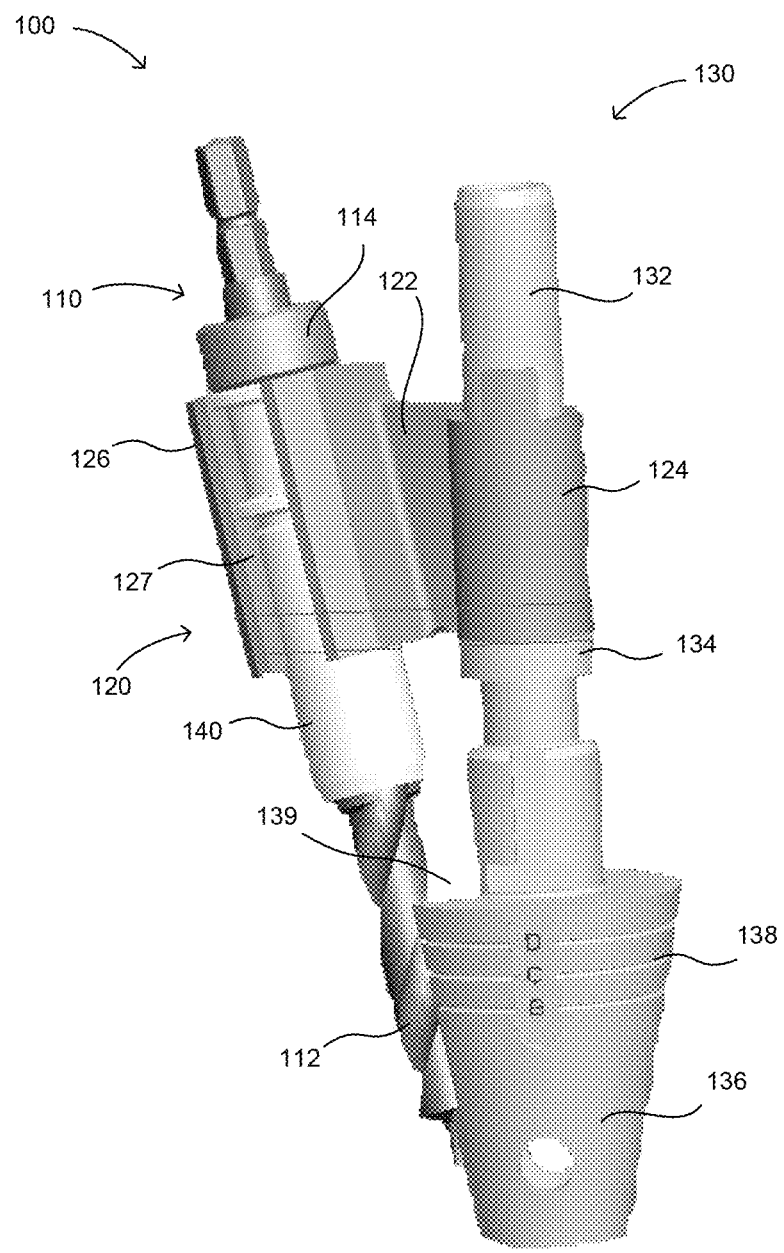
FIG. 3 is perspective view of one embodiment of a bone resection assembly.

FIG. 3 depicts a reamer assembly 100 for preparing a bone to receive void filler 10, which includes a trial 130, a reamer guide 120, a bushing 140, and a reamer 110. When implanting void filler 10, it is preferable to have the bone prepared to create a press-fit between void filler 10 and the bone such that compression of the bone promotes bony ingrowth into void filler 10. Such bone preparation can be reproducibly performed by reamer assembly 100.

Trial 130 includes a head 136 and a shaft 132. Head 136 is frustoconical to match the profile or shape of metaphyseal portion 12. Head 136 includes indicia 138, such as laser lines, to indicate the depth of head 136 in the bone. Head 136 also includes a groove 139 extending along its length to create space for cutting head 112 during the reaming process.

Reamer 110 includes a cutting head 112, a bushing 140, and a depth stop 114. Cutting head 112 is slidable within and guided by bushing 140. Depth stop 114 is located proximal to bushing 140 and during use contacts bushing 140 to indicate that cutting head 112 has reached the appropriate depth.

Reamer guide 120 includes a retaining sleeve 124 that is configured to slide over shaft 132 of trial 130. Reamer guide 120 also includes a guide collar 126 attached to retaining sleeve 124 by a flange 122 such that guide collar 126 has a longitudinal axis that is angled with respect to a longitudinal axis of retaining sleeve 124.

Guide collar 126 generally includes a slot 127 extending through a sidewall in guide collar 126. Slot 127 is in communication with a retaining channel that extends through guide collar 126. The retaining channel is sized to slidingly receive and retain bushing 140, and slot 127 is sized to allow reamer head 112, but not bushing 140, to be passed there through.

Reamer 100 is mounted to guide collar 126 by holding bushing 140 against depth stop 114 and passing cutting head 112 though slot 127 and into the retaining channel. Once cutting head 112 is in the retaining channel, bushing 140 is slid into the retaining channel where it is retained during the reaming process in which cutting head 112 is guided by bushing 140 into bone.

Figure 4:
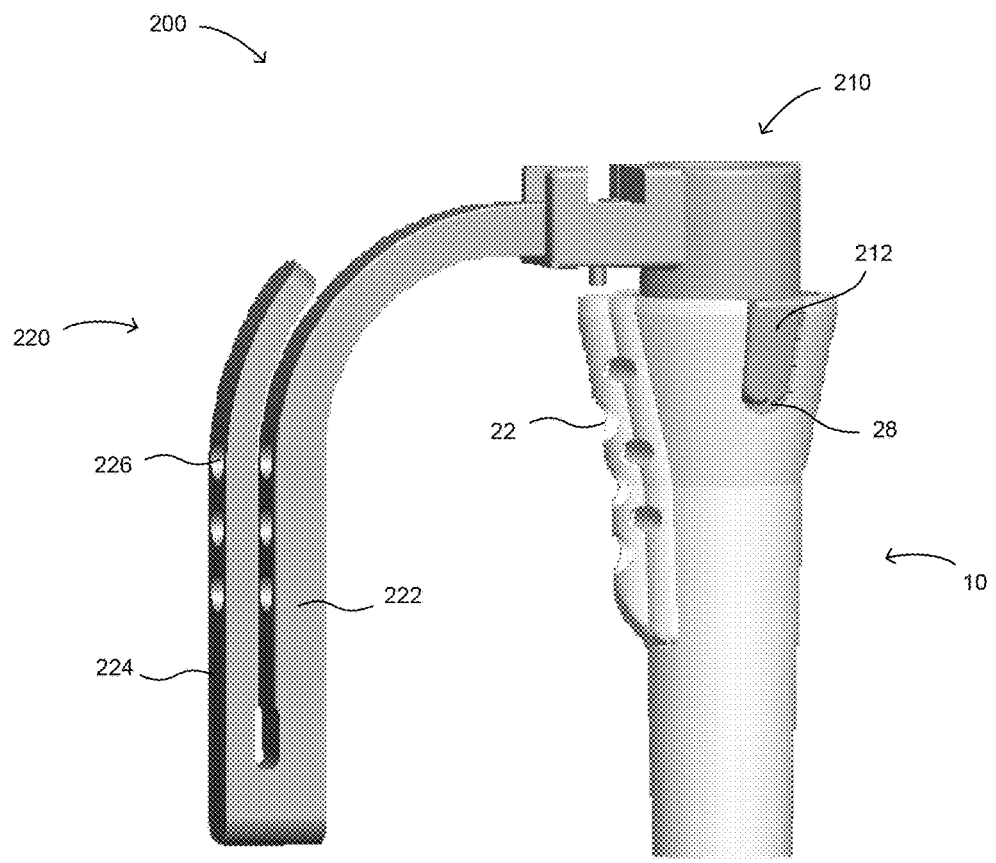
FIG. 4 is a perspective view of the void filling prosthesis of FIG. 1 and an aiming device.

FIG. 4 depicts an aiming device 200 that can be used when securing a threaded fastener to void filler 10 through bone and/or tissue. Once void filler 10 is implanted, bone and tissue may obscure the operator's view of fixation apertures 22 and 24. Aiming device 200 allows the operator to locate threaded openings 22 through such bone and tissue. Aiming device 200 generally includes a body 210 and aiming arm 220.

Body 210 may be cylindrical or frustoconical such that it fits within the channel of the metaphyseal portion. Alignment tabs 212 extend radially outwardly from body 210 so that they can engage with or slide within notches 28 within void filler 10. This engagement aligns aiming arm 220 with fixation prominence 16.

Aiming arm 220 can be connected to body 210 or in some embodiments may be integral with body 210, and generally includes a first guide portion 222 and a second guide portion 224. First guide 222 portion extends from body 210 and curves or turns in a distal direction. In one embodiment, first guide portion 222 may include an offset segment (not shown) that would be located adjacent to the aiming arm's connection to body 210. The offset segment may be offset laterally or medially to provide a clearance space for the patella and patella tendon during fixation.

First guide portion 222 also includes a plurality of guide apertures 226 that are aligned with threaded openings 22 when aiming device 200 is engaged with void filler 10. The second guide portion 224 is offset anteriorly from first guide portion 222 and also includes a plurality of guide apertures 226 that are also aligned with threaded openings 22 of void filler 10. This offset relationship helps stabilize a driving device when driving a threaded fastener into threaded opening 22.

In a wire fixation embodiment (not shown), an aiming arm may extend from body 210 in a lateral or medial direction when engaged to void filler 10 and align with passageways 24. In this embodiment, the wires may be passed through guide apertures in the aiming arm and punched or passed through the bone and through passageways 24.

In one embodiment of a method of use, void filler 10 may be utilized to reattach a bone fragment resected during a tibial tubercle osteotomy. Such attachment may be achieved by wire fixation, suture fixation, screw fixation, or the like. In a tibial tubercle osteotomy, a bone fragment underlying the tibial tubercle and patella tendon is at least partially resected so that the extensor mechanism can be moved aside to expose the primary or previously implanted prosthesis. The prosthesis is removed from the tibia, and the bone is assessed for defects. An appropriate void filler is selected based on the size and shape of the defect, and a single reamer or a series of reamers are used to prepare the void for void filler 10. After a generally frustoconical void is formed in the metaphysis with a frustoconical reamer (not shown) that corresponds with head 136 and metaphyseal portion 12, head 136 of trial 130 may be placed into the void. If the proper depth of the head, as indicated by indicia 138, cannot be reached, the bone is successively reamed until the proper depth is achieved.

Thereafter, with head 136 securely placed within the void such that groove 139 generally faces anteriorly, reamer guide 120 is slid over shaft 132 of trial 130 until retaining sleeve 124 abuts abutment surface 134. Cutting head 112 is passed through slot 127 while bushing 140 is in a proximal position about cutting head 112 such that bushing 140 is proximal of guide collar 126 as cutting head 112 is passed through slot 127. Once cutting head 112 is within the retaining channel of guide collar 126, bushing 140 is advanced distally until it is fully seated within guide collar 126. Reamer 110 is then advanced into the bone to form a resected geometry to receive fixation prominence 16.

Depending on the condition of the bone and/or the extent of the bone defect, the tibial tubercle osteotomy may remove so much anterior bone that a slot in the anterior bone extending into the bone canal is exposed. Where this occurs, anterior reaming for fixation prominence 16 may not be warranted since there may be no anterior bone to resect. If this is the case, a rongeur may be used to shape the resected bone fragment to matingly engage fixation prominence 16 when reaffixing the fragment to the tibia.

Once the void has been sufficiently shaped, void filler 10 is inserted into the bone to achieve a press-fit relationship with the bone via impaction or some other means. This impaction or other means may occur until the proximal end of void filler 10 is either flush with or below the proximal end of the tibia.

Aiming device 200 is then attached to void filler 10 by inserting body 210 into metaphyseal portion 12 and by inserting the alignment tabs 212 into the notches 28 of metaphyseal portion 12. At this point aiming arm 220 is oriented in an anterior position external to the bone and aligned with fixation prominence 16. The fragment of bone that was removed by the tibial tubercle osteotomy is placed into a mating position against the tibia and a threaded fastener is advanced through guide apertures 226 of aiming device 200, through the bone, and into threaded openings 22 of void filler 10, thereby affixing the bone fragment to the tibia and void filler 10.

Once the bone fragment and patella tendon are secured, the tibial prosthesis, which preferably includes a baseplate and a stem, is affixed to the tibia. This may be performed by placing cement or some other adhesive into the channel of void filler 10 and or around the stem, and then inserting the stem into and through the channel such that at least a portion of the stem extends from the distal end of void filler 10.

As an alternative to a threaded fastener, cerclage wires may be utilized to fix the bone fragment to the tibia. In this embodiment method of fixation, an aiming device specific to wire or suture fixation is engaged to the implanted void filler 10. Wires are advanced through the guide apertures, through the bone, through passageways 24, and back out through the bone. The free ends of the wires extending from the bone are then used to affix the bone fragment to the tibia in the usual way.

In another method of wire fixation utilizing void filler 10, void filler 10 can be inserted such that fixation prominence 16 faces posteriorly. In this embodiment, wires can be passed through the bone and passageways 24 at a posterior region of the tibia and then wrapped around the tibia to secure the bone fragment. Alternatively, the wires may be wrapped around void filler 10 prior to implantation. This may be achieved by selecting a void filler 10 that is sized to be cemented into the bone, rather than press-fit, or a void filler 10 with channels to house the wires as void filler 10 is impacted into the bone.

Turning to another method embodiment, void filler 10 may be utilized to make other repairs such as the repair of a ruptured patella tendon. In this embodiment void filler 10 is utilized in a similar fashion as with a tibial tubercle osteotomy. For example, where the patella tendon is ruptured, a bone plug and tendon allograft may be harvested and implanted into the tibia. In this embodiment, void filler 10 is implanted into the bone, aiming device 200 engaged to void filler 10, and the bone plug either fixed to void filler 10 and bone via threaded fastener or via wire fixation, as previously described.

Still other types of procedures are possible utilizing void filler 10 described herein. For example, void filler 10 may be used in procedures involving uncontained defects or other bone defects or repairs that require the use of morselized bone graft and metal mesh to contain the bone graft material. In such a procedure, void filler 10 and fixation apertures extending therein may be used to help fix the mesh to void filler 10. In this scenario, fixation prominence 16 may be a plurality of bumps each containing threaded opening 22 or passageway 24 wherein the bumps and fixation apertures may be utilized to help secure the wire mesh to the bone to facilitate a solid containment unit for the morselized bone graft, particularly as the graft material is being impacted into the bone.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone void forming assembly, comprising:
a support member having a head portion and an elongate portion extending from the head portion;
a guide member connectable to the support member and having a guide body including a channel extending therethrough and a slot extending through the guide body along a length thereof and being in fluid communication with the channel, the channel defining a body axis offset relative to an axis of the elongate portion when the guide member is connected to the support member;
a reamer having a stop member; and
a bushing slidably connected to the reamer between the stop member and a cutting head thereof and to the guide body via the channel, the bushing having an outer dimension larger than a width of the slot such that the bushing is prevented from being passed through the slot and into the channel therefrom.

2. The apparatus of claim 1, wherein the head portion is frustoconically shaped.

3. The apparatus of claim 2, wherein the head portion includes a groove extending along a side surface thereof configured to receive a portion of the reamer.

4. The apparatus of claim 2, wherein the head portion includes indicia configured to indicate a depth of the head portion when inserted into an end of a bone.

5. The apparatus of claim 1, wherein:
the guide member includes a sleeve portion receiving a portion of the elongate portion, and
the elongate portion includes an abutment surface abutting the sleeve portion at one end thereof to position the sleeve portion at a predefined location along the elongate portion.

6. The apparatus of claim 5, wherein the sleeve portion and guide body are connected to each other such that the channel is obliquely angled relative to a sleeve axis defined by the sleeve portion.

7. The apparatus of claim 1, wherein:
a portion of the reamer has an outer dimension smaller than the width of the slot such that said portion of the reamer can be passed through the slot and into the channel.

8. The apparatus of claim 1, wherein the bushing is dimensioned so as to slide into the channel from an end of the guide body.

9. A bone void forming assembly, comprising:
a support member having an end portion configured for insertion into an end of bone;
a guide member connected to the support member, the guide member having a sidewall defining a channel sized to receive the bushing and a slot extending through the sidewall so as to communicate with the channel, the bushing having an outer dimension larger than a width of the slot such that the bushing is prevented from being passed through the slot and into the channel therefrom; and
a reamer assembly connected to the support member via the bushing, the reamer assembly having a reamer and a bushing slidably connected to the reamer.

10. The apparatus of claim 9, wherein, when the reamer assembly is connected to the guide member, the reamer is slidable through the bushing along a reamer axis.

11. The apparatus of claim 10, wherein the reamer axis is offset from a support axis defined by the support member.

12. The apparatus of claim 11, wherein the reamer axis is obliquely angled relative to the support axis.

13. The apparatus of claim 9, wherein the width of the slot is sized to allow passage of a portion of the reamer therethrough and into the channel while prohibiting passage of the bushing therethrough.

14. A bone void forming apparatus, comprising:
a support member having an elongate portion;
a guide member connected to the elongate portion and having an inner surface and an outer surface defining a sidewall therebetween, the inner surface defining a channel extending through a length of the guide member, the guide member further defining a slot extending through the sidewall and being in communication with the channel;
a reamer having first and second ends and a cutting portion disposed therebetween; and
a bushing slidably connected to the reamer between the first and second ends thereof, the bushing having an outer dimension smaller than a dimension of the channel so as to allow the bushing to slide into the channel from a first end of the guide body, the outer dimension of the bushing being larger than a width of the slot such that the bushing is prevented from being passed through the slot and into the channel therefrom.

15. The apparatus of claim 14, wherein at least a portion of the reamer has a dimension smaller than a dimension of the slot so as to allow the reamer to be passed through the slot and into the channel.

16. The apparatus of claim 15, wherein the outer dimension of the bushing is smaller than a dimension of the channel.

17. The apparatus of claim 16, wherein the guide body has a body offset and obliquely angled relative to an axis of the support member.

* * * * *